United States Patent
Königsmann et al.

(10) Patent No.: US 8,975,460 B2
(45) Date of Patent: Mar. 10, 2015

(54) PROCESS FOR PREPARING ACETYLENE BY THE SACHSSE-BARTHOLOMÉ PROCESS

(75) Inventors: Lucia Königsmann, Stuttgart (DE); Maximilian Vicari, Limburgerhof (DE); Thomas Heidemann, Viernheim (DE); Dirk Großschmidt, Mannheim (DE); Jürgen Michel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 195 days.

(21) Appl. No.: 13/183,683

(22) Filed: Jul. 15, 2011

(65) Prior Publication Data
US 2012/0022308 A1 Jan. 26, 2012

Related U.S. Application Data

(60) Provisional application No. 61/365,802, filed on Jul. 20, 2010.

(51) Int. Cl.
*C07C 5/02* (2006.01)
*C07C 5/03* (2006.01)
*C07C 2/78* (2006.01)

(52) U.S. Cl.
CPC ........................ *C07C 2/78* (2013.01)
USPC ........... 585/256; 585/254; 585/264; 585/266; 585/269; 585/275; 585/277; 208/142; 208/143; 208/144

(58) Field of Classification Search
USPC ......... 585/256, 254, 264, 266, 269, 275, 277; 208/142, 143, 144
See application file for complete search history.

(56) References Cited

U.S. PATENT DOCUMENTS

| | | | | |
|---|---|---|---|---|
| 6,127,310 A | * | 10/2000 | Brown et al. | 502/339 |
| 6,127,588 A | * | 10/2000 | Kimble et al. | 585/260 |
| 2001/0001805 A1 | * | 5/2001 | Brown et al. | 585/259 |

(Continued)

FOREIGN PATENT DOCUMENTS

| | | | |
|---|---|---|---|
| DE | 10 2008 061 611 A1 | | 6/2009 |
| DE | 102008061611 A1 | * | 6/2009 |
| EP | 1 041 037 A2 | | 10/2000 |
| EP | 1 462 160 A2 | | 9/2004 |

OTHER PUBLICATIONS

DE 102008061611A1 Description—English Translation.*
Kemp, Ian C. (2007). Pinch Analysis and Process Integration—A User Guide on Process Integration for the Efficient Use of Energy (2nd Edition). Elsevier.*

(Continued)

*Primary Examiner* — In Suk Bullock
*Assistant Examiner* — Philip Louie
(74) *Attorney, Agent, or Firm* — Oblon, McClelland, Maier & Neustadt, L.L.P.

(57) ABSTRACT

A process is proposed for preparing acetylene by the Sachsse-Bartholomé process by combustion of a natural gas/oxygen mixture in one or more burners to obtain a cracking gas which is cooled in two or more stages in burner columns, each burner having one or more burner columns assigned thereto, and said cracking gas being quenched with pyrolysis oil in the first cooling stage, to obtain a low boiler fraction comprising benzene, toluene and xylene from the one or more burner columns, which is cooled with direct cooling water and separated in a phase separator into an aqueous phase and an organic phase which comprises benzene, toluene and xylene and is fully or partly introduced to the top of the one or more burner columns as a return stream, wherein the organic phase comprising benzene, toluene and xylene from the phase separator, prior to full or partial recycling to the top of the one or more burner columns, is supplied to a selective hydrogenation over a catalyst which comprises at least one platinum group metal on an inorganic metal oxide as support, comprising 0.05 to 5% by weight of platinum group metal, based on the total weight of the catalyst, and wherein the selective hydrogenation is performed at a pressure in the range from 10 to 70 bar gauge and a temperature in the range from 0 to 100° C.

10 Claims, 1 Drawing Sheet

(56) References Cited

U.S. PATENT DOCUMENTS

2003/0204120 A1* 10/2003 Bergmeister et al. ......... 585/258
2007/0125533 A1* 6/2007 Minderhoud et al. ........ 166/267

OTHER PUBLICATIONS

U.S. Appl. No. 13/292,691, filed Nov. 9, 2011, Russ, et al.

U.S. Appl. No. 13/292,777, filed Nov. 9, 2011, Grossschmidt, et al.

International Preliminary Report on Patentability and Written Opinion issued Jan. 22, 2013 in PCT/EP2011/062125 filed on Jul. 15, 2011.

U.S. Appl. No. 13/902,175, filed May 24, 2013, Vicari, et al.

* cited by examiner

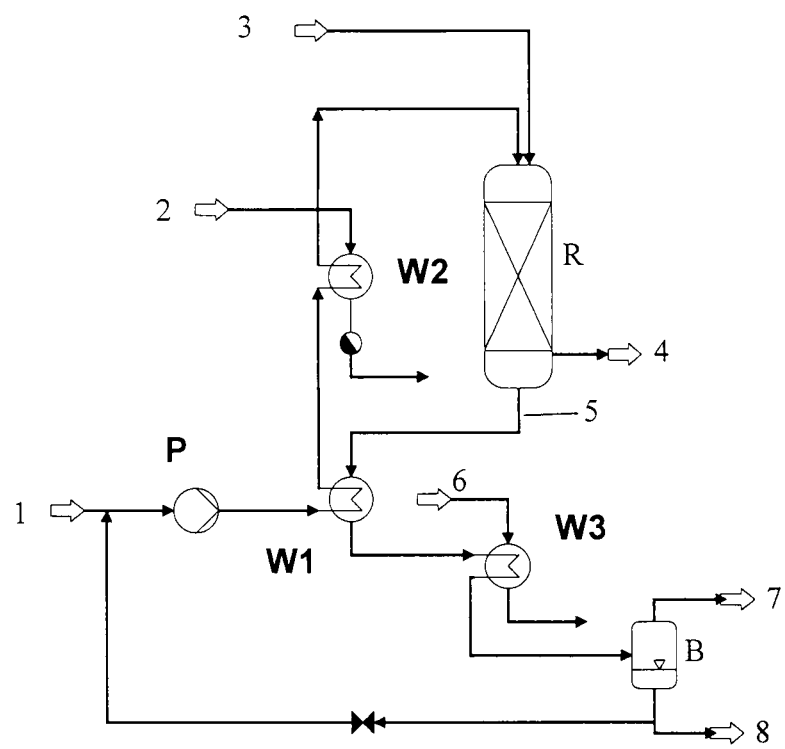

PROCESS FOR PREPARING ACETYLENE BY THE SACHSSE-BARTHOLOMÉ PROCESS

The invention relates to a process for preparing acetylene by the Sachsse-Bartholomé process.

Acetylene is a high-reactivity colorless and odorless gas. Many intermediates, for example butanediol, vinyl ethers or vinyl monomers, are prepared from acetylene. Acetylene can be obtained, for example, by the Sachsse-Bartholomé process, by combustion of a natural gas/oxygen mixture at about 1700° C. to obtain cracking gas which comprises, as by-products, synthesis gas ($H_2$/CO), $CO_2$, coke and crude naphthalene. After the combustion, the hot cracking gas is cooled in burner columns in several stages. In a first stage, the hot reaction mixture is quenched with an oil. In this first quench stage, the cracking gas is cooled to approx. 250° C. within a few milliseconds. This forms a multitude of aromatic and polycyclic compounds. About one third of these compounds are monomers, principally styrene, indene and derivatives thereof. These highly reactive monomeric compounds exhibit a high tendency to form polymers, which leads to problems with polymer deposits in certain plant parts.

In order to reduce these problems, various proposals have been made for stabilization of mixtures from acetylene preparation by addition of polymerization inhibitors. Suitable for this purpose are especially polymerization inhibitors selected from the group consisting of N-oxyls, aromatic amines, aliphatic amines, phenols and mixtures thereof, as proposed, for example, in DE 10 2008 061 611.

The problems connected to polymer deposits can, however, also be reduced or avoided by removing the polymerizable components, especially styrene and indene, from the product mixture which is obtained by quenching the cracking gas with pyrolysis oil, especially by selective hydrogenation.

It was an object of the invention to provide a technically simple and economically viable process for selective hydrogenation of components from cracking gases quenched with pyrolysis oil from acetylene preparation, which would lead to problems with polymer deposits.

The solution consists in a process for preparing acetylene by the Sachsse-Bartholomé process by combustion of a natural gas/oxygen mixture in one or more burners to obtain a cracking gas which is cooled in two or more stages in burner columns, each burner having one or more burner columns assigned thereto, and said cracking gas being quenched with pyrolysis oil in the first cooling stage, to obtain a low boiler fraction comprising styrene, indene, benzene, toluene and xylene from the one or more burner columns, which is cooled with direct cooling water and separated in a phase separator into an aqueous phase and an organic phase which comprises styrene, indene, benzene, toluene and xylene and is introduced to the top of the one or more burner columns as a return stream, wherein the organic phase comprising styrene, indene, benzene, toluene and xylene from the phase separator is supplied to a selective hydrogenation over a catalyst which comprises at least one platinum group metal on an inorganic metal oxide as support, comprising 0.05 to 5% by weight of platinum group metal, based on the total weight of the catalyst, and wherein the selective hydrogenation is performed at a pressure in the range from 1 to 40 bar and a temperature in the range from 25 to 150° C.

According to the Sachsse-Bartholomé process, acetylene is obtained by burning a natural gas/oxygen mixture in one or more burners. This provides the high reaction temperature required for the endothermic acetylene formation by partial oxidation of the natural gas used with pure oxygen.

This forms a cracking gas typically with the following composition:

| | |
|---|---|
| $H_2$ | 56% by vol. |
| $CH_4$ | 5% by vol. |
| $C_2H_2$ | 7.5% by vol. |
| CO | 26% by vol. |
| $CO_2$ | 3.5% by vol. |
| higher hydrocarbons | 1% by vol., |
| remainder nitrogen, oxygen and argon, | up to a total of 100% by vol. |

To ensure a high selectivity, it is necessary to heat natural gas and oxygen to 600° C. separately in natural gas-fired heaters. According to the mixing device and passage of the burner block, the gas mixture is partially oxidized. Thus, within a few thousandths of a second, the acetylene-containing cracking gas forms in a flame reaction at 1500 to 1700° C.

The hot cracking gas obtained is cooled in two or more burner columns, a first cooling stage with pyrolysis oil involving very abrupt quenching to approx. 240° C. Pyrolysis oil is a bottom stream from steamcrackers and consists almost exclusively of aromatic compounds.

In spite of the short residence time, a portion of the acetylene formed decomposes to hydrogen and soot, which is taken up by the quench oil.

In the burner columns, the quenched cracking gas is cooled further stepwise down to approx. 70° C. and then leaves the burner columns for further workup into the gas fractions of crude acetylene (for acetylene purification, which can be integrated into a butanediol plant), lean gas (CO/$H_2$ synthesis gas for the methanol plant) and higher acetylenes which are combusted to raise steam.

As a result of the contact of the pyrolysis oil with the hot cracking gases, cracking of the pyrolysis oil takes place, which forms coke (soot) and a multitude of aromatic and polycyclic compounds, especially benzene, toluene, ethylbenzene, m/p/o-xylenes, methylethylbenzene, trimethylbenzenes, naphthalene and mixtures thereof as nonpolymerizable components, and ethynylbenzene, styrene, 2,3,4-methylstyrenes, indene, methylindenes, dicyclopentene, ethylene, propylene, acetylene, propyne, propadiene, butene, butadiene and mixtures as polymerizable compounds.

It is therefore necessary to constantly supply fresh pyrolysis oil from the steamcracker.

In order to always ensure that the soot content does not exceed a given maximum concentration, it is necessary to constantly regenerate a portion of the pyrolysis oil in the quench circuit, in natural gas-fired regenerating ovens, i.e. to separate it into acetylene coke and pyrolysis oil. This also carbonizes a portion of the pyrolysis oil. The acetylene coke is discharged and constitutes a saleable product.

The last cooling step in the burner columns is effected with a mixture which comprises benzene, toluene and xylene and forms as a low boiler fraction in the quenching of the cracking gas with pyrolysis oil.

Subsequently, the cracking gas is cooled to approx. 40° C. with direct cooling water, separated in a phase separator into an aqueous phase and an organic phase which comprises, as well as benzene, toluene and xylene, also a high proportion of styrene and indene, with the consequence that this would lead to polymerization in the upper region of the burner columns and in the direct cooling water circuit.

Therefore, before this stream is recycled to the top of the burner columns, the components which would lead to polymerization, especially styrene and indene, are supplied to a selective hydrogenation. For this purpose, the entire stream comprising benzene, toluene and xylene from the plant is run through the selective hydrogenation. The stream now stabilized by selective hydrogenation can be recycled as return stream to the top of the burner columns or passed into the aromatics recovery step.

The organic phase comprising styrene, indene, benzene, toluene and xylene from the phase separator preferably has the following composition:
8 to 18% by weight of styrene,
5 to 10% by weight of indene,
15 to 20% by weight of the sum of ortho-, para- and meta-xylene,
15 to 20% by weight of toluene and
8 to 10% by weight of benzene,
where the sum of the components is 100% by weight.

A typical composition for the organic phase from the phase separation connected downstream of the quench stage with pyrolysis oil is:
8 to 10% by weight of benzene,
15 to 20% by weight of toluene,
1 to 5% by weight of ethylbenzene,
15 to 20% by weight of m/p/o-xylenes,
5 to 10% by weight of methylethylbenzene,
1 to 5% by weight of trimethylbenzenes,
0 to 1% by weight of butadiene,
5 to 10% by weight of ethynylbenzene,
14 to 18% by weight of styrene,
0 to 5% by weight of 2,3,4-methylstyrene,
5 to 10% by weight of indene,
0 to 4% by weight of methylindene,
0 to 4% by weight of dicyclopentene and
1 to 5% by weight of naphthalene,
where the sum of the components adds up to 100% by weight.

The aromatic compounds used in the process according to the invention thus originate from the oxidation of natural gas, which takes place in parallel with the preparation of acetylene from natural gas and oxygen, and from the quench process in which at least a portion of the quench oil used is thermally cracked.

In the present context, selective hydrogenation of the organic low boiler fraction comprising styrene, indene, benzene, toluene and xylene from the phase separator connected downstream of the quench stage with pyrolysis oil is understood to mean the hydrogenaton of styrene, indene and derivatives thereof while preserving the aromatic rings, and the hydrogenation of dienes to the corresponding monoenes.

The selective hydrogenation is performed over a supported catalyst which comprises an inorganic metal oxide as a support and, as an active material, at least one platinum group metal, where the proportion of the platinum group metal is 0.05 to 5% by weight, based on the total mass of the catalyst. The selective hydrogenation is performed at a pressure in the range from 10 to 70 bar gauge, preferably at a pressure in the range from 20 to 40 bar gauge, more preferably at 30 bar gauge. The temperature of the selective hydrogenation is in the range from 25 to 150° C., preferably 40 to 120° C., preferably 60 to 100° C., especially 80 to 100° C.

The catalyst used comprises at least one platinum group metal on an inorganic metal oxide as a support, where the content of platinum group metal is 0.05 to 5% by weight, preferably 0.1 to 2.5% by weight, especially 0.2 to 1% by weight, especially 0.2 to 0.4% by weight. The platinum group metal used is more preferably palladium. Up to 20% by weight, preferably up to 10% by weight, of the palladium may be replaced by other platinum group metals. The catalyst more preferably comprises only palladium as the active metal. The support may be selected from any desired suitable inorganic metal oxides. The catalyst support used is preferably aluminum oxide, titanium dioxide, zirconium oxide, silicon dioxide or a mixture of two or more thereof. The support more preferably comprises aluminum oxide, and is especially an $Al_2O_3$ support, for example a γ-alumina support.

The catalyst support has a porosity of preferably 0.2 to 1.0 ml/g, more preferably 0.3 to 0.6 ml/g. The median pore volume is preferably in the range from 5 to 20 nm, preferably 7.5 to 12.5 nm.

Since the noble metal catalyst can be deactivated by carbon monoxide, the organic phase comprising styrene, indene, benzene, toluene and xylene from the phase separator is preferably depleted, before being supplied to the selective hydrogenation, of residues of carbon monoxide present therein down to 5 ppm by weight, based on the total weight of the organic phase from the phase separator, more preferably down to 1 ppm by weight, based on the total weight of the organic phase from the phase separator.

The depletion of carbon monoxide is preferably effected by stripping with hydrogen.

The depletion of carbon monoxide can also preferably be effected by distillation.

In the process according to the invention, the catalyst can be deactivated over prolonged periods, for example when relatively large amounts of styrene are present in the starting mixture. The catalyst can be regenerated by known processes. For example, the catalyst can be purged with nitrogen and then heated under nitrogen to temperatures in the range from 100 to 300° C., more preferably 150 to 250° C. Subsequently, nitrogen can be replaced by superheated steam, and it can be heated further to temperatures of 300 to 400° C. On attainment of this temperature, a portion of the steam can be replaced by air, for example 1 to 10% by volume. Thereafter, the catalyst bed can be cooled, in which case steam is again replaced by nitrogen. Before further use of the catalyst, it should be reduced once again. The regeneration of the catalyst is preferably performed at a pressure in the range from 1 to 5 bar, especially 2 to 4 bar.

In the process according to the invention, a particularly favorable position in the plant for preparing acetylene by the Sachsse-Bartholomé process and workup of the gas mixture obtained here for the selective hydrogenation of high-reactivity monomers which are present therein and lead to problems with polymer deposits.

In the plant, a large recycle stream of typically 40 m$^3$/h, which comprises predominantly benzene, toluene and xylene, is introduced at the top of the one or more burner columns as a return stream. Into this stream is mixed a comparatively small stream of typically about 500 kg/h of mixture which comprises benzene, toluene and xylene and high-reactivity monomers, especially styrene and indene, and forms in the quenching of the cracking gas with pyrolysis oil. This means that the stream which is supplied to the selective hydrogenation comprises the high-reactivity polymerizable compounds obtained in the quenching with pyrolysis oil in high dilution. As a result, the strongly exothermic selective hydrogenation leads to only a small temperature increase of generally not more than 5 K, and is found to be relatively simple as a result, especially because no special measures are required for extraction of the heat of hydrogenation. This would otherwise be necessary in order to prevent the hydrogenation reactor from running away. The process is therefore particularly advantageous in safety and energy terms, and is gentle on the catalyst.

The selective hydrogenation is preferably performed in a hydrogenation reactor which is started up with a liquid which is inert under the reaction conditions of the selective hydrogenation, especially benzene, toluene or a selectively hydrogenated benzene, toluene and xylene mixture, and the mixture which comprises styrene, indene, benzene, toluene and xylene and is to be subjected to the selective hydrogenation is gradually supplied thereto. This procedure avoids the risk of a runaway reaction as a result of an excessive temperature increase in the hydrogenation reactor.

Preference is given to performing the process in such a way that hydrogen is supplied to the hydrogenation reactor in such a way that an at least 10% hydrogen excess, based on the sum of the chemical hydrogen consumption and the hydrogen dissolved in the hydrogenation reactor under the reaction conditions of the selective hydrogenation, is ensured. More particularly, a partial hydrogen pressure of at least 5 bar, preferably of at least 18 bar, and of not more than 50 bar, in the hydrogenation reactor should be ensured.

The hydrogen excess ensures, inter alia, flow through the hydrogenation reactor and the discharge of inerts, and ensures that the catalyst remains active.

The invention is illustrated in detail hereinafter with reference to a working example and to a FIGURE.

WORKING EXAMPLE

A low boiler fraction comprising benzene, toluene and xylene from a combustion column, which has been obtained by cooling a cracking gas by quenching with pyrolysis oil, comprising 17 area % of styrene and 11 area % of indene, of 3.5 g/h, was supplied to a hydrogenation reactor which was operated at a temperature of 60° C., was with a catalyst H0-55, i.e. an eggshell catalyst comprising 0.27% by weight of palladium on γ-alumina, a BET surface area of 240 m$^2$/g and a pore volume of 0.45 ml/g.

The hydrogenation reactor was a tubular reactor with an internal diameter of 6 mm, and which was equipped in the inlet region with metal spheres in a heating zone and then with the above-described catalyst.

The catalyst was activated with hydrogen at elevated temperature in the hydrogenation reactor before startup, and for this purpose reduced at 120° C. and 10 ml/h of hydrogen at ambient pressure for 12 h.

The reaction was started up at 60° C./20 bar for 53 h. In the course of this, it was found that, surprisingly, the catalyst is deactivated rapidly (styrene in the product from 0 to 0.25 area %).

After 53 operating hours, the temperature was increased to 80° C. and, over the course of 500 h, a >98% conversion of styrene to ethylbenzene to >96% conversion of indene to indane were obtained.

After 500 h, the pressure was increased to 30 bar and the reaction was run for a further 1600 h, in the course of which the conversion of styrene to ethylbenzene remained at >98%, or >96% from indene to indane.

After a total of 2153 h, the temperature was increased to 100° C. In the course of this, the conversion of styrene to ethylbenzene rose to >99%, and >98% from indene to indane. After 2700 h, the reaction was stopped without clear deactivation of the catalyst.

The liquid samples were analyzed by GC. The column used was 150 m Pertocol FD 1 μm, ID 0.25 mm, 35° C./20 min, 2° C./min to 140° C., 4° C./min to 250° C./40 min.

The sole FIGURE, FIG. 1, shows the schematic diagram of a preferred plant for selective hydrogenation by the process according to the invention.

After a carbon monoxide removal to a residual carbon monoxide content of below 5 ppm by weight, the feed stream comprising styrene, indene, benzene, toluene and xylene, stream 1, was brought to the required reaction pressure of approx. 3 bar gauge by means of the feed pump P. This stream is supplied to a countercurrent heat exchanger W1, preheated therein and then supplied to the peak heater W2, in which the required reactor inlet temperature of 80° C. at the Start Of Run (SOR) up to 140° C. at the End Of Run (EOR). This feed stream is introduced, together with hydrogen, stream 3, to the hydrogenation reactor R from the top downward under quantitative control via a catalyst bed.

It is possible to use two hydrogenation reactors connected in parallel in order to undertake an in situ regeneration. For instance, one reactor may always be in operation, while the second reactor is regenerated.

In the bottom of the hydrogenation reactor R, the liquid phase, the selective hydrogenated mixture comprising benzene, toluene and xylene, separates from the excess gas phase which, even under EOR conditions, consists to an extent of more than 95% by volume of hydrogen. In order to keep the catalyst active, at least 10% of the chemical hydrogen consumption should be run out of the hydrogenation reactor R under pressure control as offgas, stream 4. This also adjusts the pressure in the reactor. The reactor offgas, stream 4, is supplied to the cracking gas system of the acetylene plant. The product stream 5, which is drawn off from the bottom of the hydrogenation reactor R, is expanded to approx. 4 bar gauge in the separator B after cooling in the countercurrent heat exchanger W1 with the feed stream and further cooling to approx. 40° C. in the product cooler W3, which is operated with cooling water, stream 6. The liquid obtained, the selectively hydrogenated product mixture comprising benzene, toluene and xylene, is drawn off as stream 8 and distributed between the burner columns of the plant as the return stream. The excess can be supplied to an aromatics recovery step.

The separator B also serves to start up the selective hydrogenation with the existing holdup of the acetylene plant with mixture comprising a high content of benzene, toluene and xylene monomers. For this purpose, the separator B is, for example, filled with toluene or pyrolysis gasoline full raffinate, and pumped in circulation through the selective hydrogenation plant by means of the feed pump P. The mixture comprising a high content of benzene, toluene and xylene monomers from the separating vessels of the acetylene plant is then added slowly, such that no temperature increase of more than 10 K occurs in the reactor. Mixture comprising selectively hydrogenated benzene, toluene and xylene is discharged to the acetylene plant. Thus, the entire holdup of the acetylene plant comprising benzene, toluene and xylene is gradually put through the selective hydrogenation plant.

The invention claimed is:

1. A process for preparing acetylene by the Sachsse-Bartholomé process by burning a natural gas/oxygen mixture in one or more burners to obtain a cracking gas which is cooled in two or more stages in burner columns, each burner having one or more burner columns assigned thereto, and said cracking gas being quenched with pyrolysis oil in the first cooling stage, to obtain a low boiler fraction comprising styrene, indene, benzene, toluene and xylenes from the one or more burner columns, which is cooled with direct cooling water and separated in a phase separator into an aqueous phase and an organic phase which consists of:
   8 to 18% by weight of styrene;
   5 to 10% by weight of indene,
   a total of 15 to 20% by weight of the sum of ortho-, para- and meta-xylene,
   15 to 20% by weight of toluene and
   8 to 10% by weight of benzene,
   where the sum of all components adds up to 100% by weight;

and is introduced to the top of the one or more burner columns as a return stream, and recovering acetylene;
wherein the organic phase consisting of styrene, indene, benzene, toluene and xylenes from the phase separator is supplied to a selective hydrogenation over a catalyst which comprises at least one platinum group metal on an inorganic metal oxide as support, comprising 0.05 to 5% by weight of platinum group metal, based on the total weight of the catalyst, and wherein the selective hydrogenation is performed at a pressure in the range from 1 to 40 bar and a temperature in the range from 25 to 150° C. to selectively hydrogenate styrene, indene and derivatives thereof while preserving the aromatic rings, such that the selective hydrogenation of indene proceeds at a conversion of >96%.

2. The process according to claim 1, wherein the catalyst comprises palladium on aluminum oxide, titanium dioxide, zirconium oxide, silicon dioxide or mixtures thereof as a support.

3. The process according to claim 1, wherein the selective hydrogenation is performed in a fixed bed.

4. The process according to claim 1, wherein the selective hydrogenation is performed in a hydrogenation reactor which is started up with an inert liquid, especially benzene, toluene or a selectively hydrogenated benzene/toluene/xylene mixture, and to which the organic phase to be subjected to selective hydrogenation is gradually supplied.

5. The process according to claim 1, wherein the organic phase consisting of styrene, indene, benzene, toluene and xylenes from the phase separator, before being supplied to the selective hydrogenation, is depleted of residues of carbon monoxide present therein down to 5 ppm by weight, based on the total weight of the organic phase from the phase separator.

6. The process according to claim 5, wherein the depletion of carbon monoxide is effected by stripping with hydrogen.

7. The process according to claim 5, wherein the depletion of carbon monoxide is effected by distillation.

8. The process according to claim 1, characterized by thermal integration in the selective hydrogenation, by utilizing the heat of the product stream from the selective hydrogenation for preheating of the organic phase consisting of styrene, indene, benzene, toluene and xylenes and is to be subjected to the selective hydrogenation.

9. The process according to claim 1, wherein hydrogen is supplied to the hydrogenation reactor in such a way that an at least 10% excess, based on the sum of the chemical hydrogen consumption and the hydrogen dissolved in the hydrogenation reactor under the reaction conditions of the selective hydrogenation, is ensured.

10. The process according to claim 5, wherein the organic phase consisting of styrene, indene, benzene, toluene and xylenes from the phase separator, before being supplied to the selective hydrogenation, is depleted of residues of carbon monoxide present therein down to 1 ppm by weight, based on the total weight of the organic phase from the phase separator.

* * * * *